United States Patent [19]

Wong et al.

[11] Patent Number: 5,499,979
[45] Date of Patent: Mar. 19, 1996

[54] DELIVERY SYSTEM COMPRISING KINETIC FORCES

[75] Inventors: Patrick S.-L. Wong, Palo Alto; Felix Theeuwes; James B. Eckenhoff, both of Los Altos, all of Calif.

[73] Assignee: Alza Corporation, Palo Alto, Calif.

[21] Appl. No.: 209,033

[22] Filed: Mar. 10, 1994

Related U.S. Application Data

[63] Continuation-in-part of Ser. No. 905,714, Jun. 29, 1992, abandoned, which is a continuation of Ser. No. 551,711, Jul. 10, 1990, abandoned, which is a continuation of Ser. No. 283,631, Dec. 13, 1988, Pat. No. 4,957,494, which is a continuation-in-part of Ser. No. 270,160, Nov. 14, 1988, abandoned, which is a continuation-in-part of Ser. No. 66,906, Jun. 25, 1987, Pat. No. 4,874,388.

[51] Int. Cl.$^6$ .................................................. A61K 9/22
[52] U.S. Cl. ................................ 604/891.1; 604/890.1; 604/892.1; 424/438; 514/30
[58] Field of Search ............................ 424/438, 422, 424/457, 468, 471–473; 604/131, 890.1, 891.1, 892.1

[56] References Cited

U.S. PATENT DOCUMENTS

| | | | |
|---|---|---|---|
| 1,736,078 | 11/1929 | Haas . | |
| 2,620,061 | 12/1952 | Uxa | 206/42 |
| 2,853,206 | 9/1958 | Uxa | 221/229 |
| 3,410,455 | 11/1968 | Haas | 221/229 |
| 3,565,284 | 2/1971 | Hinterreiter | 221/229 |
| 3,656,483 | 4/1972 | Rudel | 128/264 |
| 3,844,445 | 10/1974 | Haas | 221/229 |
| 3,845,770 | 11/1974 | Theeuwes et al. | 128/260 |
| 3,845,882 | 11/1974 | Haas | 221/279 |
| 3,995,631 | 12/1976 | Higuchi et al. | 128/260 |
| 3,995,632 | 12/1976 | Nakano et al. | 128/260 |
| 4,034,756 | 7/1977 | Higuchi et al. | 128/260 |
| 4,111,202 | 9/1978 | Theeuwes | 128/260 |
| 4,177,256 | 12/1979 | Michaels et al. | 424/22 |
| 4,203,441 | 5/1980 | Theeuwes | 128/260 |
| 4,220,152 | 9/1980 | Dresback | 128/250 |
| 4,220,153 | 9/1980 | Dresback | 128/260 |
| 4,251,506 | 2/1981 | Laby | 424/19 |
| 4,264,573 | 4/1981 | Powell et al. | 424/19 |
| 4,265,874 | 5/1981 | Bonsen et al. | 424/15 |
| 4,320,759 | 3/1982 | Theeuwes | 128/260 |
| 4,326,522 | 4/1982 | Guerrero et al. | 128/260 |
| 4,344,929 | 8/1982 | Bonsen et al. | 424/15 |
| 4,350,271 | 9/1982 | Eckenhoff | 222/386.5 |
| 4,381,780 | 5/1983 | Holloway | 604/892 |
| 4,410,328 | 10/1983 | Theeuwes | 604/892 |
| 4,449,983 | 5/1984 | Cortese et al. | 604/892 |
| 4,454,108 | 6/1984 | Iida et al. | 424/472 |
| 4,475,916 | 10/1984 | Himmelsten | 424/473 |
| 4,578,263 | 3/1986 | Whitehead | 424/15 |
| 4,578,264 | 3/1986 | Stricker et al. | 424/37 |
| 4,589,575 | 5/1986 | Rigberg | 221/198 |
| 4,595,583 | 6/1986 | Eckenhoff et al. | 424/15 |
| 4,612,008 | 9/1986 | Wong et al. | 604/892 |

(List continued on next page.)

FOREIGN PATENT DOCUMENTS

| | | | |
|---|---|---|---|
| 0230654 | 8/1987 | European Pat. Off. | A61K 9/22 |
| 0246819 | 11/1987 | European Pat. Off. | A61K 9/00 |
| 2133122 | 1/1972 | Germany . | |
| 3021848 | 11/1980 | Germany | B01J 4/02 |
| 2155787 | 10/1985 | United Kingdom | A61K 9/66 |
| 8400282 | 2/1984 | WIPO | A23K 1/00 |
| 8600519 | 1/1986 | WIPO | A61D 7/00 |
| 0174815 | 3/1986 | WIPO | 424/438 |

OTHER PUBLICATIONS

"Using the ALZET® Osmotic Pumps to Generate a Circadian Rhythm" and Technical Tip No. 17, ALZA Corporation, May 1986.

"American Heritage Dictionary" (2nd Edition), 1982 p. 937.

*Primary Examiner*—C. Fred Rosenbaum
*Assistant Examiner*—Chalin Smith
*Attorney, Agent, or Firm*—Felissa H. Cagan; Paul L. Sabatine; Steven F. Stone

[57] ABSTRACT

A dispenser for use in a fluid environment which is capable of delivery of plurality of drugs in any desired delivery pattern or profile.

6 Claims, 4 Drawing Sheets

U.S. PATENT DOCUMENTS

| | | | |
|---|---|---|---|
| 4,612,186 | 9/1986 | Eckenhoff et al. | 424/15 |
| 4,623,330 | 11/1986 | Laby et al. | 604/53 |
| 4,624,847 | 11/1986 | Ayer et al. | 424/15 |
| 4,627,850 | 12/1986 | Deters et al. | 604/892 |
| 4,642,230 | 2/1987 | Whitehead et al. | 424/15 |
| 4,723,958 | 2/1988 | Pope et al. | 604/890.1 |
| 4,764,359 | 8/1988 | Lemelson | 424/457 |
| 4,874,388 | 10/1989 | Wong et al. | 604/891.1 |
| 4,957,494 | 9/1992 | Wong et al. | 604/891.1 |
| 5,008,112 | 4/1991 | DePrince et al. | 424/468 |
| 5,023,088 | 6/1991 | Wong et al. | 604/891.1 |

DELIVERY SYSTEM COMPRISING KINETIC FORCES

RELATED PATENT APPLICATIONS

This application is a continuation-in-part of U.S. Ser. No. 07/905,714, filed Jun. 29, 1992, now abandoned, which is a continuation of U.S. Ser. No. 07/551,711, filed Jul. 10, 1990, now abandoned, which is a continuation of U.S. Ser. No. 07/283,631, filed Dec. 13, 1988, now U.S. Pat. No. 4,957,494, issued Sep. 18, 1990, which is a continuation-in-part of U.S. Ser. No. 07/270,160, filed Nov. 14, 1988, now abandoned, which is a continuation-in-part of U.S. Ser. No. 07/066,906, filed Jun. 25, 1987, now U.S. Pat. No. 4,874,388, issued Oct. 17, 1989. This application is with U.S. Ser. No. 07/495,825, filed Mar. 19, 1990, now U.S. Pat. 5,023,088, issued, Jun. 11, 1991.

FIELD OF THE INVENTION

This invention relates to patterned drug delivery. More particularly, this invention relates to patterned drug delivery by means of a plurality of drug delivery layers. Still more particularly, but without limitation thereto, this invention relates to delivery of multi-agents orally or in other media in a pre-programmed delivery profile.

DEFINITION OF TERMS

The expressions "active agent" and "drug" are used interchangeably and as used herein broadly include any compound, composition of matter or mixture thereof, that can be delivered from the system to produce a beneficial and useful result. This includes pesticides, herbicides, germicides, biocides, algicides, rodenticides, fungicides, insecticides, anti-oxidants, plant growth promoters, plant growth inhibitors, preservatives, anti-preservatives, disinfectants, sterilization agents, catalysts, chemical reactants, fermentation agents, foods, food supplements, nutrients, cosmetics, drugs, vitamins, sex sterilants, fertility inhibitors, fertility promoters, air purifiers, microorganism attenuators and other agents that benefit the environment of use.

The terms "active agent" and "drug" as used herein further includes any physiologically or pharmacologically active substance that produces a localized or systemic effect or effects in animals, including warm blooded mammals, humans and primates, avians, domestic household, sport or farm animals such as sheep, goats, cattle, horses and pigs, or is administered to laboratory animals such as mice, rats and guinea pigs, to fish, reptiles, zoo and wild animals. The active drug which can be delivered includes inorganic and organic compounds including without limitation, those materials that act upon the central nervous system such as hypnotics and sedatives, psychic energizers, tranquilizers, anticonvulsants, muscle relaxants, anti-parkinson agents, analgesics, anti-inflammatory, local anesthetics, muscle contractants, anti-microbials, anti-malarials, hormonal agents including contraceptives, sympathomimetrics, diuretics, anti-parasites, neoplastics, hypoglycemics, nutritional, fats, ophthalmic, electrolytes and diagnostics agents.

The term "drug layer" as used herein includes wax formulations, solid cores, tablets, pellets and elongated tablets where the height to diameter ratio exceeds one, with or without excipients for controlling erosion.

As used herein the expression "external fluid" includes water and biological fluids.

BACKGROUND OF THE INVENTION

The concept of patterned drug delivery covers a broad range of systems from time release capsules whose components have coatings which erode at different rates, to controlled release rate tablets which operate by osmosis.

Despite the development of the art however, there remains a continuing need for improved methods and systems for providing controlled drug release profiles on a larger scale.

SUMMARY OF THE INVENTION

An object of this invention is to provide sequential timing and dispensing of delivery layers containing the same or different active agents.

Another object of this invention is to provide both a novel and useful agent formulation delivery system that is self-contained, self-powered and also represents an improvement in the delivery art.

These and other objects are demonstrated by the present invention wherein a drug dispenser for use in a fluid containing environment comprises a rigid housing, a plurality of movable drug layers filling a portion of the housing, a fluid activated driving member for displacing the drug layers filling the remainder of the housing and a drug outlet means.

BRIEF DESCRIPTION OF THE DRAWINGS

The invention will be described in further detail with reference to the accompanying drawings wherein.

DESCRIPTION OF THE PREFERRED EMBODIMENT

Figure 1:
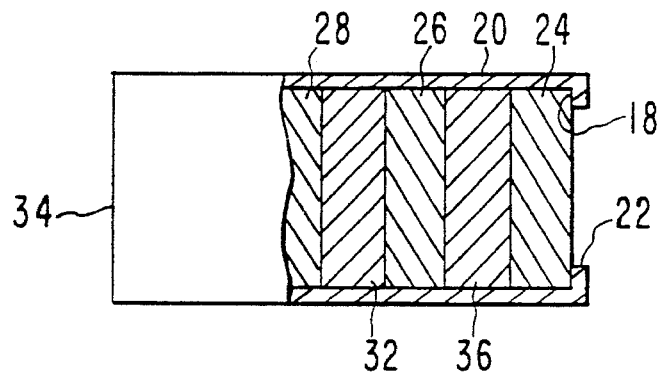
FIG. 1 is a partial cross-sectional view of the dispenser of this invention, illustrating one embodiment of the dispensing configuration.

This invention can provide a variety of drug delivery profiles including, but not limited to, pulsed delivery of a single drug or drug formulation, pulsed delivery of a sequence of different drugs or drug formulations, pulsed delivery of one drug or drug formulation superimposed on continuous delivery of a different drug or drug formulation, and simultaneous continuous delivery of several drugs or drug formulations.

This invention is particularly suited to the delivery of pharmacologically active peptides and protein anabolic hormones such as growth promoting hormones related to the endocrine system comprising porcine growth promoting hormone, bovine growth promoting hormone, equine growth promoting hormone, ovine growth promoting hormone, human growth promoting hormone, growth promoting hormones derived by extraction and concentration from pituitary and hypothalamus glands, growth promoting hormones produced by recombinant DNA methods, bovine growth promoting hormone as described in *Nucleic Acid Res.*, Vol. 10, p 7197 (1982), ovine growth promoting hormone as described in *Arch. Biochem. Biophys.*, Vol. 156, p 493 (1973), and porcine growth promoting hormone as described in *DNA*, Vol. 2, pp 37, 45 (1983). Also included are polypeptides such as growth hormone, somatropin, somatotropin, somatomedin-C, gonadotropic releasing hormone, follicle stimulating hormone, luteinizing hormone, LH-RH, growth hormone releasing factor, gonadotropin releasing factor, insulin, colchicine, chorionic gonadotropin, oxytocin, vasopressin, adrenocorticotrophic hormone, epidermal growth factor, prolactin, somatostatin, cosyntropin, lypressin, polypeptides such as thyrotropin releasing hormone, thyroid stimulating hormone, secretin pancreozymin, enkephalin, glucagon, and the like. The active agents and their dosage unit amounts are known to the art in *The Pharmacological Basis of Therapeutics*, by Gilman. Goodman, Rail and Murad, 7th Ed., (1985) published by MacMillan Publishing Co., NY; in *Pharmaceutical Sciences*, Remington, 17th Ed., (1985) published by Mack Publishing Co., Easton, Pa.; and in U.S. Pat. No. 4,526,938.

The drug delivery system or dispenser of this invention is designed to deliver a drug or drug formulation by displacement of a plurality of discrete longitudinally aligned individual drug layers by the linear expansion of a fluid activated driving member. It is comprised of a dispensing component and a driving component, representative embodiments of which are disclosed herein. FIGS. 1, 6, 7 and 10 illustrate various embodiments of the dispensing component suitable for use in the dispenser of this invention. These configurations can be combined with various embodiments of the driving component, representative embodiments of which are illustrated in FIGS. 2–5, and of the housing structure itself, shown in FIGS. 1, 2, 4, 7 and 11–15.

The dispensing and driving component designs are for use in a fluid-containing environment and are merely exemplary of the numerous embodiments suitable for use in this invention. The portion of the housing adjacent to the dispenser component is of a material which can be either semi-permeable or substantially impermeable to the passage of external fluid. Typical impermeable materials include polyethylene, polyethylene terephthalate (Mylar), plasticized polyvinyl chloride, metal-foil polyethylene laminates, neoprene rubber, natural gum rubber, and Pliofilm (rubber hydrochloride). These materials are additionally flexible, insoluble and chemically compatible with the active agent contained in the layers positioned therein, and, in the instance of providing a drug or like depot within the body of a living organism, are biologically inert, non-irritating to body tissues and non-allergenic. Additional suitable materials include polystyrene, polypropylene, polyvinyl chloride, reinforced epoxy resin, polymethylmethacrylate, etc., sheet metal (e.g., aluminum, copper, steel, etc.), galvanized pipe, or styrene/acrylonitrile copolymer. Again, for drug depot applications, the same are advantageously biologically inert, non-irritating to body tissue and non-allergenic. Suitable semipermeable materials include all cellulosic polymers such as cellulose acetates, ethylcellulose, methylcellulose, cellulose acetate butyrate, cellulose acetate propionate, etc. or blends of an impermeable material and a hydrophilic polymer or a low molecular weight water soluble enhancer to render the material semipermeable.

Many other materials including those which are biologically acceptable are suitable for fabrication of the impermeable portion of the housing. While this portion has previously been described as being insoluble under the conditions and in the environment of intended use, it is also within the scope of the invention that such materials be insoluble only during the period of said intended use; thereafter dissolving away in the environment of the device. Thus, a dispenser is here contemplated which is unaffected by its environment, solubility-wise, at the situs of use, or which is only slightly soluble during the period of intended use, such that once its active agent content has been removed it will then dissolve or erode away leaving no objectionable residue or empty container at the said situs of use.

The portion of the housing adjacent to the driving component may be of the same material. However, several of the driving component designs operate by the imbibition of external fluid. For those particular embodiments, the portion of the housing adjacent thereto, must be semipermeable and allow passage of external fluid. Suitable materials will be described with reference to the specific driving member embodiments.

The dispensing component shown in FIG. 1 is comprised of a rigid housing member 20. Housing 20 is also designed with an outlet means, exit port 22. A plurality of movable discrete layers 24, 26, 28, 30 and 32, are aligned within the housing 20. This configuration is merely illustrative and the dispenser may have numerous drug layers in excess of the number shown in FIG. 1.

The drug layers can erode or disintegrate and can be in the form of a wax formulation, solid core or tablet. The layers can immediately dissolve upon exposure to fluid or they may erode slowly with or without the presence of excipients for controlling erosion. The layers can be designed in a multitude of ways to provide a specific drug delivery profile. Layers which immediately dissolve provide pulsed drug delivery while layers which erode provide continuous delivery for the duration of the layer.

As stated above, one embodiment consists of layers which slowly disintegrate upon contact with the external fluid. These layers may contain a biologically acceptable solid surfactant which is capable of slow dispersion in the environmental fluid. In another embodiment, the layers may be susceptible to erosion upon contact with the external fluid and contain a fluid insoluble wax such as stearic acid, paraffin wax or beeswax, and a non-ionic surfactant such as ethoxylated alcohols and polyether, both being biologically acceptable. In still another embodiment, the layers may be effervescent and provide drug delivery in a finely dispersed form. This is accomplished by the addition of a solid basic compound capable of evolving carbon dioxide in the presence of an acid in the environment of use. Suitable basic compounds are disclosed in U.S. Pat. No. 4,265,874, incorporated herein by reference.

The drug layers of this invention may also contain binders, lubricants, and optionally excipients such as compounds to stabilize the drug or to facilitate erosion. An example of a suitable composition as contemplated by this invention is about 80–95 wt % drug, about 2–3 wt % binder, about 0.1–5 wt % lubricant, about 1–15 wt % excipient to facilitate disintegration or erosion and about 1–6 wt % to stabilize the drug.

Materials suited for use in formulating the layers of this invention are well known in the art and are fully described in texts such as *Pharmaceutical Sciences*, Remington, Chapter 87. Binders which impart cohesive qualities include, without limitation, starch, gelatin, agar, natural and synthetic gums, carboxycellulose, carboxymethylcellulose, methylcellulose, polyvinyl alcohol, polyvinyl pyrrolidone, polyethylene glycol, cellulose acetate, polyurethane and waxes. Lubricants serve numerous purposes including improving the rate of flow of the granulated particles, and facilitating the actual manufacture of the layers. Suitable lubricants include, without limitation, talc, starch, zinc stearate, aluminum stearate, magnesium stearate, calcium stearate, boric acid, sodium chloride, paraffin, stearic acid, low melting point waxes, hydrogenated vegetable oils and saturated fatty acid esters. The layers may also include a disintegrant such as lightly cross-linked polyvinyl pyrrolidone, corn starch, potato starch, Veegum®, bentonite and citrus pulp. It may also be desirable to include stabilizers for the drug. These include without limitation, sodium bisulfite and histadine HCl.

The drug layer composition may also be modified to include about 0.1–5 wt % of a surfactant and/or about 0.01–2 wt % of an anti-oxidant, for example. Suitable surfactants include, without limitation, sorbitan monostearate, polysorbate 80 USP [polyoxyethylene (20) sorbitan monooleate], and polyoxyethylene 4 stearate. Suitable anti-oxidants include, without limitation, tertiary butyl-4-methoxyphenol (mixture of 2- and 3-isomers), 2,6-ditertiary butyl-p-cresol, propyl gallate, 6-ethoxy-1,2-dihydro-2,2,4-trimethylquinoline (ethoxyquin) and nordihydroguaiaretic acid (NDGA).

The driving member 34 operates to displace the layers towards the exit port 22. As the layers come into contact with the exit and are exposed to the external fluid, they begin to erode in a controlled or semi-controlled fashion. The exit port 22 is fashioned with a lip 36 which acts to keep the layers intact within the housing 20 as it erodes. This provides continuous delivery of drug until layer 24 is completely eroded. Once layer 24 is completely eroded, linear displacement pushes layer 30 through the housing 20 so that it comes into contact with exit 22.

In one embodiment, layers 24, 26, 28, 30 and 32 contain different drugs or drug formulations. In another embodiment, layers 24, 26 and 28 may contain the same or different drugs or drug formulations and layers 30 and 32 can be comprised of an inert hydrophobic gel such as petrolatum. This would provide an "off" period during which time no drug is being delivered. Additionally, the layers may be effervescent to shorten the pulse time.

For rumenal systems, an important criteria is that the system remain in the rumen of an animal over a prolonged period of time. This is accomplished by placement of a density element within the dispenser. The housing 20 itself, may be the density element. Alternately, unit 28 can be a density element, placed so as to remain within the housing 20 after all of the drug layers have eroded.

The density element suitable for use in the dispenser of this invention must be dense enough to retain the dispenser in the rumenreticular sac of a ruminant, The presence of a density element allows the dispenser to remain in the rumen over a prolonged period of time rather than letting it pass into the alimentary tract and be eliminated therefrom. As the dispenser remains in the rumen, a beneficial agent can be delivered to the ruminant at a controlled rate over an extended period of time. Generally, a density element will have a density of from about 0.8 to 8, or higher, with the density in a presently preferred embodiment exhibiting a specific gravity of from about 2.2 to 7.6. For the ruminants cattle and sheep, it is presently preferred that the density element exhibit a density such that there is a resulting dispenser density of about 3. Materials that have a density that can be used for forming a suitable density element include iron, iron shot, iron shot coated with iron oxide, iron shot magnesium alloy, steel, stainless steel, copper oxide, a mixture of cobalt oxide and iron powder, and the like.

Exemplary of drugs that are soluble or very soluble in water and can be delivered by the dispenser systems of this invention include prochlorperazine edisylate, ferrous sulfate, aminocaproic acid, potassium chloride, enitabas, mecamylamine hydrochloride, procainamide hydrochloride, amphetamine sulfate, benzphetamine hydrochloride, isoproterenol sulfate, methamphetamine hydrochloride, phenmetrazine hydrochloride, bethanechol chloride, metacholine chloride, pilocarpine hydrochloride, atrophine sulfate, methscopolamine bromide, isopropamide iodide, tridihexethyl chloride, phenformin hydrochloride, methylphenidate hydrochloride, and mixtures thereof.

Exemplary of agents that have limited solubility or are very slightly soluble, or insoluble in water and biological fluids that can be delivered by the dispenser systems of this invention include diphenidol, meclizine hydrochloride, prochlorperazine maleate, thiethylperazine maleate, anisindione, diphenadione, erythrityl tetranitrate, digoxin, isoflurophate, reserpine, azetazolamide, methazolamide, bendroflumethiazide, chlorpropamide, tolazamide, chlormadinone acetate, phenaglycodol, allopurinol, aluminum aspirin, methotrexate, acetyl sulfisoxazole, erythromycin, and mixtures thereof, steroids including corticosteroids such as hydrocortisone, hydrocorticosterone acetate, cortisone acetate and triamcinolone, anhydrogens such as methyltesterone, esterogenic steroids such as 17β-estradiol, ethinyl estradiol, ethinyl estradiol 3-methyl ether and estradiol, progestational steroids such as prednisolone, 17α-hydroxyprogesterone acetate, 19-nor-progesterone, norethindrone, progesterone, norethynodrel, and the like.

The drug can also be in the various chemical and physical forms such as uncharged molecules, molecular complexes, pharmacologically acceptable acid addition and base addition salts such as hydrochlorides, hydrobromides, sulfate, laurylate, palmitate, phosphate, nitrate, borate, acetate, maleate, tartrate, oleate and salicylate. For acidic drugs, salts of metals, amines or organic cations, for example quaternary ammonium can be used. Derivatives of drugs such as esters, ethers and amides can be used alone or mixed with other drugs. Also, a drug which is water insoluble can be used in a form that on its release from the dispenser, is converted by enzymes, hydrolyzed by body pH or other metabolic processes to the original form, or to a biologically active form.

The dispensing configuration of FIGS. 1, 6, 7 and 10, can be combined with any of the driving members illustrated in FIGS. 2–5 to provide a tailored drug delivery system.

Figure 2:
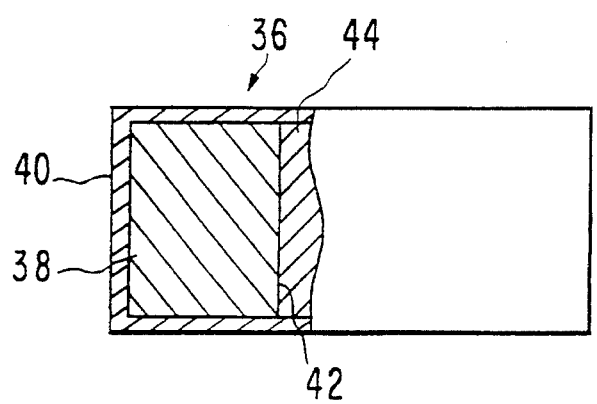
FIG. 2 is a partial cross-sectional view of one embodiment of the driving member for the dispenser of this invention, utilizing a hydrophilic expandable member.

FIG. 2 illustrates a driving member system 36 utilizing an expandable driving member 38 comprised of an external fluid insoluble, external fluid swellable composition. Member 38 is encased in housing 40 which is a semipermeable membrane substantially permeable to the passage of an external fluid and substantially impermeable to the passage of any ingredients contained in member 38. The driving member 38 is positioned adjacent to one of the drug layers at interface 42.

External fluid is imbibed through the housing 40 by the expandable hydrophilic member 38 in a tendency toward osmotic equilibrium, to continuously swell and expand member 38. Member 38 expands while maintaining an intact immiscible boundary at interface 42, defined by the surface of drug layer 44 and expandable member 38.

Expandable member 38 has a shape that corresponds to internal shape of housing 40 and is preferably made from a hydrogel composition. The hydrogel composition is non-cross-linked or optionally cross-linked and it possesses osmotic properties, such as the ability to imbibe an external fluid through semipermeable housing 40, and exhibit an osmotic pressure gradient across semipermeable housing 40 against a fluid outside the dispenser system. The materials used for forming the swellable, expandable member 38 are polymeric materials neat, and polymeric materials blended with osmotic agents that interact with water or a biological fluid, absorb the fluid and swell or expand to an equilibrium state. The polymer exhibits the ability to retain a significant fraction of imbibed fluid in the polymer molecular structure. The polymers in a preferred embodiment are gel polymers that can swell or expand to a very high degree, usually exhibiting a 2 to 50 fold volume increase. The swellable, hydrophilic polymers, also known as osmopolymers, can be noncross-linked or lightly cross-linked. The cross-links can be covalent, ionic or hydrogen bonds with the polymer possessing the ability to swell in the presence of fluid, and when cross-linked it will not dissolve in the fluid. The polymer can be of plant, animal, or synthetic origin. Polymeric materials useful for the present purpose include poly (hydroxyalkyl methacrylate) having a molecular weight of from 5,000 to 5,000,000; poly (vinylpyrrolidone) having a molecular weight of from 10,000 to 360,000; anionic and cationic hydrogels; poly (electrolyte) complexes; poly (vinyl alcohol) having a low acetate residual; a swellable mixture of agar and carboxymethyl cellulose; a swellable composition comprising methyl cellulose mixed with a sparingly cross-lined agar; a water swellable copolymer produced by a dispersion of finely divided copolymer of maleic anhydride with styrene, ethylene, propylene, or isobutylene; water swellable polymer of N-vinyl lactams; swellable sodium salts of carboxy methyl cellulose; and the like.

Other gelable, fluid imbibing and retaining polymers useful for forming the hydrophilic, expandable driving member 38 include pectin having a molecular weight ranging from 30,000 to 300,000; polysaccharides such as agar, acacia, karaya, tragacanth, algins and guar; Carbopol® acidic carboxy polymer and its salt derivatives; polyacrylamides; water swellable indene maleic anhydride polymers; Good-rite® polyacrylic acid having a molecular weight of 80,000 to 200,000 Polyox® polyethylene oxide polymers having a molecular weight of 100,000 to 7,500,000; starch graft copolymers; Aqua-Keep® acrylate polymers with water absorbability of about 400 times its original weight; diesters of polyglucan; a mixture of cross-linked polyvinyl alcohol and poly (N-vinyl-2-pyrrolidone); poly (ethylene glycol) having a molecular weight of 4,000 to 100,000; and the like; In a preferred embodiment, the expandable member 38 is formed from polymers and polymeric compositions that are thermoformable. Representative polymers possessing hydrophilic properties are known in U.S. Pat. Nos. 3,865,108, 4,002,173, 4,207,893, 4,220,152, 4,327,725, 4,350,271, all of which are incorporated herein by reference and in Scott et al, *Handbook of Common Polymers*, CRC Press, Cleveland, Ohio (1971).

The osmotically effective compound that can be blended homogeneously or heterogeneously with the swellable polymer, to form a driving member, are the osmotically effective solutes that are soluble in fluid imbibed into the swellable polymer, and exhibit an osmotic pressure gradient across the semipermeable housing 40 against an external fluid. Osmotically effective compounds are known also as osmagents. Osmotically effective osmagents useful for the present purpose include magnesium sulfate, magnesium chloride, sodium chloride, lithium chloride, potassium sulfate, sodium sulfate, mannitol, urea, sorbitol, inositol, sucrose, glucose and the like. The osmotic pressure in atmospheres, atm, of the osmagents suitable for the invention will be greater than zero atm, generally from 8 atm up to 500 atm, or higher.

Representative materials for forming the semipermeable housing include without limitation, semipermeable homopolymers, semipermeable copolymers, and the like. In one embodiment typical materials include cellulose esters, cellulose monoesters, cellulose diesters, cellulose triesters, cellulose ethers, and cellulose ester-ethers, mixtures thereof, and the like. These cellulose polymers have a degree of substitution, D.S., on their anhydroglucose unit form greater than 0 up to 3 inclusive. By "degree of substitution" is meant the average number of hydroxyl groups originally present on the anhydroglucose unit that are replaced by a substituting group, or converted into another group. The anhydroglucose unit can be partially or completely substituted with groups such as acyl, alkanoyl, aroyl, alkyl, alkenyl, alkinyl, alkoxy, halogen, carboalkyl, alkylcarbamate, alkylcarbonate, alkylsufonate, alkylsulfamate, and like semipermeable polymer forming groups.

The semipermeable materials typically include a member selected from the group consisting of cellulose acylate, cellulose diacylate, cellulose triacylate, cellulose acetate, cellulose diacetate, cellulose triacetate, mono-, di- and tri-cellulose alkanylates, mono-, di- and tri-alkenylates, mono-, di- and tri-aroylates, and the like. Exemplary polymers including cellulose acetate having a D.S. of 1.8 to 2.3 and an acetyl content of 32 to 39.9%; cellulose diacetate having a D.S. of 1 to 2 and an acetyl content of 21 to 35%; cellulose triacetate having a D.S. of 2 to 3 and an acetyl content of 34 to 44.8% and the like. More specific cellulosic polymers include cellulose propionate having a D.S. of 1.8 and a propionyl content of 38.5%; cellulose acetate propionate having an acetyl content of 1.5 to 7% and a propionyl content of 39 to 42%; cellulose acetate propionate having an acetyl content of 2.5 to 3%; an average propionyl content of 39.2 to 45% and a hydroxyl content of 2.8 to 5.4%; cellulose acetate butyrate having a D.S. of 1.8, and acetyl content of 13 to 15%, and a butyryl content of 34 to 39%; cellulose acetate butyrate having an acetyl content of 2 to 29.5%; a butyryl content of 17 to 53%, and a hydroxyl content of 0.5 to 4.7%; cellulose triacylates having a D.S. of 2.9 to 3 such as cellulose trivalerate, cellulose trilaurate, cellulose tripalmitate, cellulose trioctanoate, and cellulose tripropionate; cellulose diesters having a D.S. of 2.2 to 2.6 such as cellulose disuccinate, cellulose dipalmitate, cellulose dioctanoate, cellulose dicarpylate; cellulose propionate morpholinobutyrate; cellulose acetate butyrate; cellulose acetate phthalate; and the like; mixed cellulose esters such as cellulose acetate valerate, cellulose acetate succinate, cellulose propionate succinate, cellulose acetate octanoate, cellulose valerate palmitate, cellulose acetate heptonate, and the like. Semipermeable polymers are known in U.S. Pat. No. 4,007,407, and they can be made by procedures described in *Encyclopedia of Polymer Science and Technology*, Vol. 3, pages 325–354, Interscience Publishers, Inc., New York, (1964).

Additional semipermeable polymers include cellulose acetaldehyde; dimethyl cellulose acetate; cellulose acetate ethylcarbamate; cellulose acetate methylcarbamate; cellulose dimethylaminoacetate; a cellulose composition comprising cellulose acetate and hydroxypropyl methylcellulose; a composition comprising cellulose acetate and cellulose acetate butyrate; a cellulose composition comprising cellulose acetate butyrate and hydroxypropyl methylcellulose; semipermeable polyamides; semipermeable polyurethanes; semipermeable polysulfanes; semipermeable sulfonated polystyrenes; crosslinked, selectively semipermeable polymers formed by the coprecipitation of a polyanion and a polycation as disclosed in U.S. Pat. Nos. 3,173,876, 3,276,586, 3,541,005, 3,541,006 and 3,546,142, all of which are incorporated herein by reference; selectively semipermeable silicon rubbers; semipermeable polymers as disclosed by Loeb and Sourirajan in U.S. Pat. No. 3,133,132, incorporated herein by reference; semipermeable polystyrene derivatives; semipermeable (polysodiumstyrenesulfonate); semipermeable poly (vinylbenzyltrimethyl) ammonium chloride; semipermeable polymers exhibiting a fluid permeability of $10^{-1}$ to $10^{-7}$ (cc.mil/cm$^2$ hr-atm) expressed as per atmosphere of hydrostatic or osmotic pressure difference across a semipermeable wall. The polymers are known in the art in U.S. Pat. Nos. 3,845,770, 3,916,899 and 4,160,020, all of which are incorporated herein by reference; and in J. R. Scott and W. J. Roff, *Handbook of Common Polymers*, CRC Press, Cleveland, Ohio (1971).

Other materials that can be used to form the semipermeable housing for imparting flexibility and elongation properties to the wall, for making the housing less to non-brittle and to render tear strength include phthalate plasticizers such as dibenzyl phthalate, dihexyl phthalate, butyl octyl phthalate, straight chain phthalates of six to eleven carbons, diisononyl phthalate, diisodecyl phthalate, and the like. The plasticizers include nonphthalates such as citric acid esters, triacetin, dioctyl azelate, epoxidized tallate, triisoctyl trimellitate, triisononyl trimellitate, sucrose acetate isobutyrate, epoxidized soybean oil, and the like. The amount of plasticizer in the housing when incorporated therein, is about 0.01 to 20% by weight, or higher.

Figure 3:
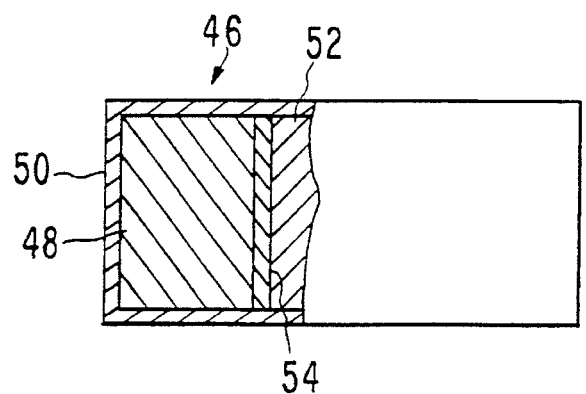
FIG. 3 is a partial cross-sectional view of a second embodiment of the driving member for the dispenser of this invention, utilizing an osmotically effective solute.

FIG. 3 illustrates a driving member 46 utilizing an osmotically effective solute. The osmotically effective solute is in solution 48 which is retained within a rigid housing 50 comprised of a semipermeable membrane substantially permeable to the passage of an external fluid and substantially impermeable to the passage of the osmotically effective solute contained in solution 48. The solution 48 is separated from the drug layers 52 for example, by means of a flexible membrane 54. The ability of driving member 46 to displace the drug layers, 52 for example, housed within a dispenser depends upon the osmotic pressure generated by the solution 48 of the osmotically effective solute confined within housing 50. This solution exhibits an osmotic pressure gradient against fluid in the environment into which the dispenser is placed, and is preferably a saturated aqueous salt solution. To maintain the solution saturated and therefore to achieve a constant osmotic pressure throughout operation of the dispenser, the housing containing the solution also contains excess solute in solid form. Various osmotically effective solutes can be used. These include magnesium sulfate, magnesium chloride, sodium chloride, potassium sulfate, sodium carbonate, sodium sulfite, sodium sulfate, sodium bicarbonate, potassium acid sulfonate, calcium bicarbonate, potassium acid phosphate, raffinose, tartaric acid, succinic acid, calcium succinate, calcium lactate and magnesium succinate. The excess solid solute can be in the form of dispersed particles or preferably in the form of a pellet. The solution can initially be a solution of the same or of an osmotically effective solute different than the solid excess solute.

Figure 4:
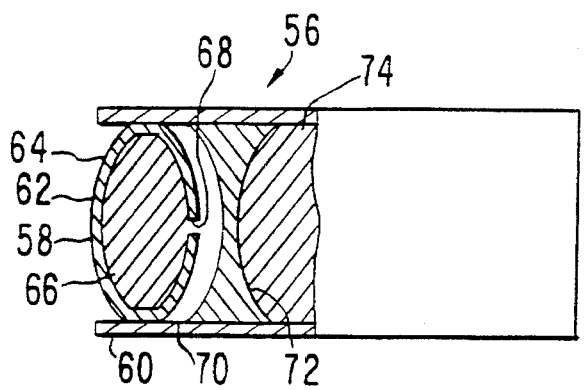
FIG. 4 is a partial cross-sectional view of another embodiment of the driving member for the dispenser of this invention, utilizing an elementary osmotic pump.

FIG. 4 illustrates a driving member 56 which is similar in operation to that of FIG. 3. An elementary osmotic pump 58 such as that disclosed in U.S. Pat. No. 3,845,770, incorporated herein by reference, is held rigidly in place in the impermeable housing 60 being exposed to the environment at surface 62. External fluid is imbibed through the semipermeable wall 64 by the osmotically effective solute 66 contained within the pump 58. As the osmotic pressure within the pump 58 increases, solution (external fluid and osmotic solute) is forced through the orifice 68 into chamber 70, thereby exerting pressure on piston 72 which subsequently moves through the housing 60 to dispense the drug layers 74 contained therein. In order for this driving member to be operable, the wall of the housing 60 immediately surrounding the pump 58, must be impermeable to the passage of fluid so that external fluid does not enter chamber 70. Therefore, use of driving member 56 mandates that the housing be at least in part of an impermeable composition.

Figure 5:
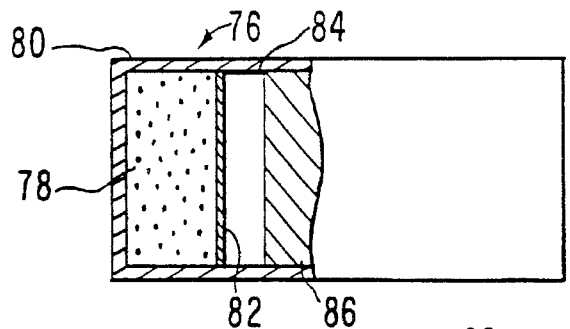
FIG. 5 is a partial cross-sectional view of another embodiment of the driving member for the dispenser of this invention, utilizing a gas generating composition.

FIG. 5 illustrates a driving member 76 which operates by means of a gas generating composition 78. Housing 80 is made of a semipermeable material which is substantially impermeable to the passage of gas generating composition 78, has a low permeability to the passage of an internally generated gas and is substantially permeable to the passage of an external fluid. Membrane 82 is made of a semipermeable material which is substantially impermeable to the passage of gas generating composition 78 and substantially permeable to the passage of a generated gas. Its main function is to keep the gas generating composition 78 apart from the drug layers contained in the dispenser.

In operation, external fluid is imbibed through housing 80 to continuously wet and dissolve the gas generating composition 78, causing it to react and produce a large volume of gas. This gas expands and passes through membrane 82, filling the space 84. This action correspondingly causes pressure to be exerted on the drug layer 86 which thereby pushes this and the other layers contained therein, through the housing 80.

Gas generating composition 78 consists essentially of a dry compound or an anhydrous mixture of compounds that when intimately contacted by an external fluid that enters the housing 80, generates a gas that exerts a pressure to drive the dispensing system. The composition 78 comprises a preferably solid acidic material, and a preferably solid basic material that dissolve and react in the presence of fluid that enters the housing 80. This composition may be in powder, crystalline, granular or layered form. Alternately, the gas generating composition may be present homogeneously or heterogeneously dispersed within a matrix. The matrix is a polymer permeable to the passage of external fluid and permeable to the passage of the generated gas. The rate of gas generated in this embodiment is governed by the rate of fluid passage through the polymer coupled with the rate of fluid passage through the housing. Suitable materials are disclosed in U.S. Pat. No. 4,203,441, incorporated herein by reference.

Figure 6:
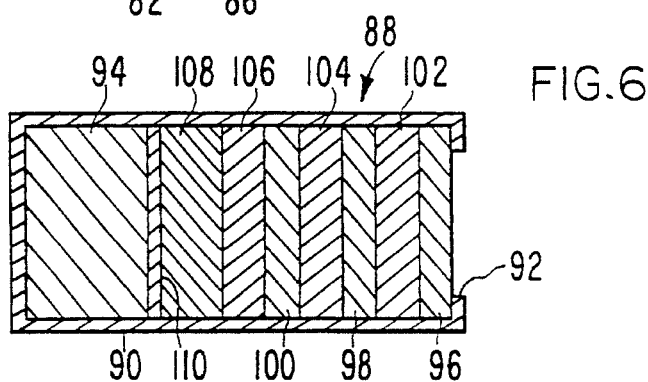
FIG. 6 is a cross-sectional view of one embodiment of the dispenser of this invention capable of delivering a plurality of discrete drug layers alternating with drug/wax formulations, and having a hydrogel driving member.

FIG. 6 illustrates an embodiment which combines the delivery methods of erosion and osmotic bursting, and is explained in detail by the following example.

EXAMPLE I

The dispenser 88 shown in FIG. 6 is especially suited for use as a rumenal bolus for the treatment of liver flukes, endoparasites and ectoparasites. Different drugs are needed to treat endo-and ectoparasites than are needed to treat liver flukes. Additionally, treatment for parasites must be continuous while that for liver flukes may be pulsed, i.e. timed to the appropriate stage in the life cycle. Therefore, separate treatments and dosage forms are required to treat these conditions.

The housing 90 is injection molded, having an exit port 92 at one end and a driving member 94 at the opposite end. The housing is filled with a plurality of discrete drug layers 96, 98 and 100. These layers are separated by drug wax formulation layers 102, 104 and 106. The housing also contains a density element 108 which may be monolithic, multilayered or particulate in nature. The driving member 94 may be any of the embodiments disclosed herein. Especially suitable is the osmotic system of FIG. 3 using a NaCl suspension.

The drug layers 96, 98 and 100 are for the treatment of liver flukes. Suitable drugs include without limitation, bithionol sulfoxide, oxyclozanide, clioxanide, niclofolan, nitroxinil, rafoxanide, benzimidazole and diamfenetide. These units osmotically burst upon exiting from the exit port 92 and therefore provide for immediate release of the drug, which will continue to be delivered for about 24 hours. The drug wax formulation layers 102, 104 and 106 are for the treatment of endoparasites and ectoparasites. A suitable formulation comprises about 12–18 weight percent ivermectin suspended in wax.

The driving member 94 is designed to allow the dispenser 88 to operate in a linear fashion. In operation, the driving member 94 imbibes external fluid through the semipermeable portion of housing 90. The NaCl suspension 94 expands and exerts pressure on flexible membrane 110 which correspondingly begins to exert pressure on element 108. Thus, the dispensing movement begins.

First, drug layer 96 which is positioned adjacent to exit port 92, is forced out of the dispenser 88 and bursts, thereby providing the environment with a pulse of drug for treatment of liver flukes. The bursting of drug layer 96 and the continuous operation of the driving member 94 linearly displace the ivermectin wax formulation 102 slowly through the exit port 92 to provide constant plasma levels of ivermectin.

This is followed by bursting of drug layer 98 and so forth until the dispenser 88 is depleted of all drug layers and wax formulation layers. The pulses of drug for the treatment of liver flukes will not interfere with the constant plasma concentrations of ivermectin since ivermectin has a half life of 3–3.5 days. An important parameter is the duration of the ivermectin layers. Each layer needs to last 21–30 days for effective treatment of endo- and ectoparasites, and must be designed accordingly.

Figure 7:
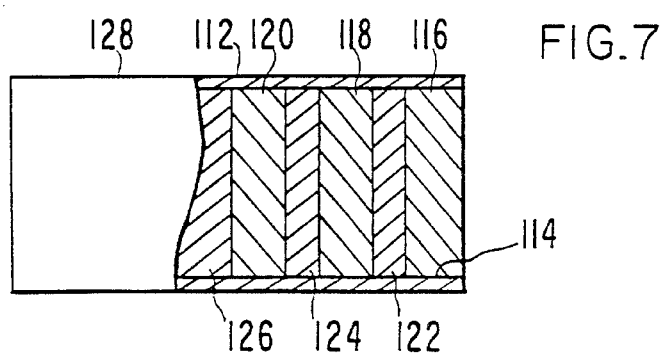
FIG. 7 is a partial cross-sectional view of the dispenser of this invention, illustrating another embodiment of the dispensing configuration.

The dispensing configuration shown in FIG. 7 illustrates yet another embodiment of the invention. This configuration is comprised of a rigid housing 112 designed with an outlet means, exit port 114. A plurality of movable discrete layers 116, 118, 120, 122, 124 and 126, are aligned within the housing 112. The six layers shown are merely illustrative and the actual system may have layers in excess of the number shown.

Drug layers 116, 118 and 120 are of a different composition from layers 122, 124 and 126. Drug layers 116, 118 and 120 are hydrophilic in nature and are solid at storage conditions. The drug can be mixed with an osmotic agent or solute, such as those described above with reference to FIG. 3. When the drug layer 116 comes into contact with the external fluid, it immediately dissolves, thereby delivering the drug contained therein, in a pulsed manner. Drug/osmotic agent layer 116 is separated from drug/osmotic agent layer 118 by a solid or semisolid hydrophobic layer 122 which is immiscible with the drug/osmotic agent layers and which slowly erodes upon contact with the environment.

Layers 122, 124 and 126 may contain the same drug or a different drug than the drug/osmotic agent layers 116, 118 and 120. The slow erosion process would provide continuous drug delivery for a set time period. Alternately, layers 122, 124 and 126, may not contain any drug and therefore would provide an "off" period for the system, during which no drug would be delivered.

Instead of containing an osmotic agent, drug layers 116, 118 and 120 can be comprised of a drug and a thermo-responsive composition. In this manner, these layers would exhibit solid-like properties at room temperature of 21° C., and within a few centigrade degrees thereof. Likewise, these layers would have a melting point that approximates mammalian body temperatures of 37° C., and within a few centigrade degrees thereof. The term "thermo-responsive" as used for the purpose of this invention in a preferred embodiment denotes the physical-chemical property of a composition agent carrier to exhibit solid, or solid-like properties at temperatures up to 31° C., and become fluid, semi-solid or viscous when disturbed by heat at temperatures from 31° C., usually in the range of 31° C. to 45° C. Suitable materials are disclosed in U.S. Pat. No. 4,595,583 incorporated herein by reference. In this embodiment, layers 166, 168 and 170 would still be a solid or semisolid composition which is immiscible with the drug/thermo-responsive composition layers.

In operation, the dispenser of FIG. 7 can deliver pulses of drug alternating with continuous delivery of drug or alternating with "off" periods, during which time no drug is delivered, depending on whether or not the erodible layers 122, 124 and 126 contain drug.

The driving member 128 operates to linearly displace the layers towards the exit port 114. As drug layer 116 comes into contact with the exit 114 it is fluid either because it contains an osmotic agent which has formed a solution with the external fluid or because it contains a heat sensitive agent which is fluid due to the temperature of the environment of use. Drug layer 116 rapidly disintegrates when it reaches the exit 114. Next is layer 122 which is held intact within the housing 112, as it slowly erodes. Depending on whether or not drug is contained in layer 122, erosion may provide continuous drug deliver or an "off" period. Once layer 122 is completely eroded, layer 118 is exposed and so forth until the system is depleted of layers.

The usefulness of the dispenser of FIG. 7 as a pulsatile multi-layer delivery system is best illustrated with reference to the following example.

EXAMPLE II

The dispenser of FIG. 7 is especially suited for control of helminth infections in ruminants, cattle in particular. A first set of drug layers, 116, 118 and 120 are comprised of 85 weight percent Hapadex® (Schering-Plough Corporation), an anthelmintic agent for cattle, and 15 weight percent Ac-Di-Sol (brand names of croscarmellose sodium, FMC Corporation), a disintegrating agent.

The alternating or second set of layers 122, 124 and 126 are comprised of 80 weight percent Fischer Wax (a microfine micronized hard wax), 15 weight percent high molecular weight hydroxypropylmethylcellulose (mol. wt. about 300,000) and 5 weight percent low molecular weight hydroxypropylmethylcellulose (mol. wt. about 7000).

Figure 8:
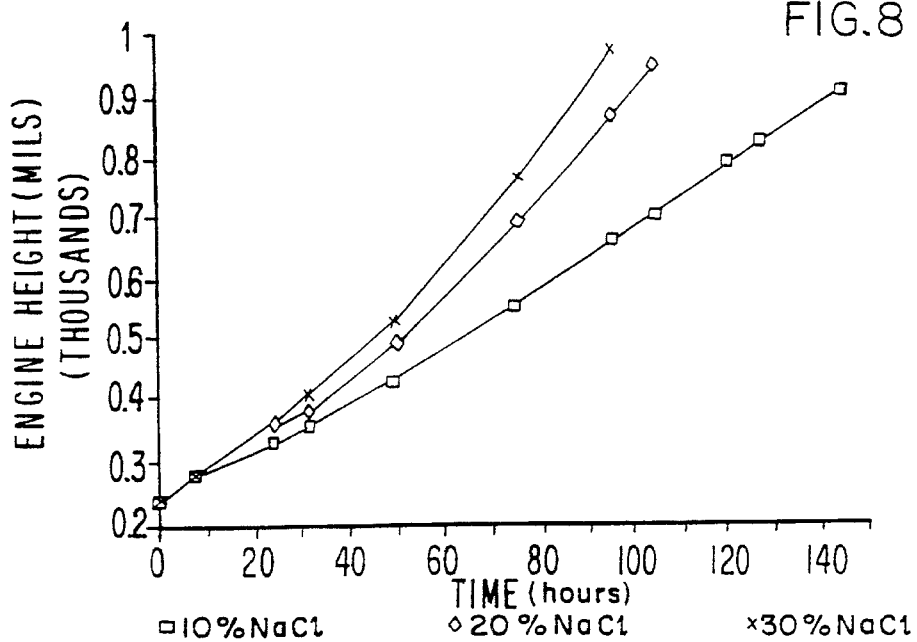
FIG. 8 is a graph depicting the expansion of the driving member in relation to the NaCl content.

The driving member 128 is like that of FIG. 2 and is an osmotic layer comprised of a mixture of a high molecular weight sodium carboxymethyl cellulose and sodium chloride. By proper adjustment of the NaCl content, the expansion of the osmotic layer (driving member 128) can likewise be adjusted. FIG. 8 provides expansion (engine height) versus time data for varied NaCl content compositions: 10, 20 and 30 weight percent. Linear expansion is obtainable with a 10% NaCl content. Increasing growth is attainable by increasing the NaCl content to 30%, as is evidenced by FIG. 8.

Figure 9:
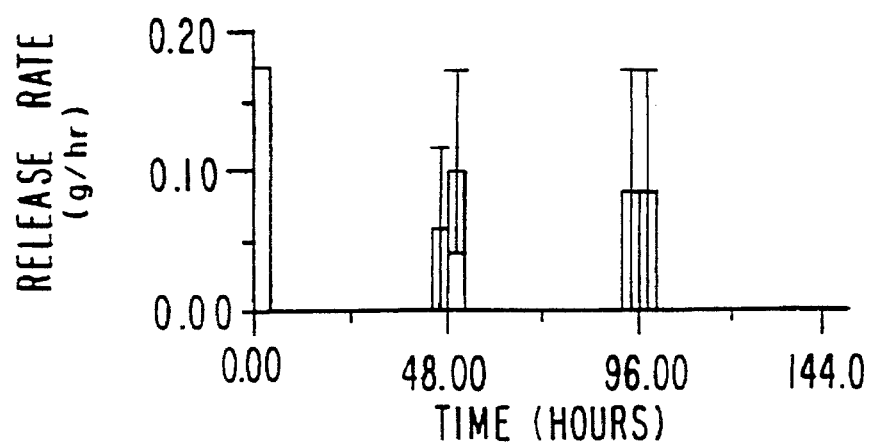
FIG. 9 is a graph of the drug release rate profile of the dispenser of FIG. 7.

FIG. 9 illustrates the release rate profile attainable with the dispenser of FIG. 7. When drug layer 116 is delivered, a pulse of drug is initially delivered at t=0 hours. This is followed by the slow erosion (about 2 days in duration) of non-drug containing layer 122, whereupon drug layer 118 is exposed and delivers a second drug pulse at t=48 hours. Once again, this is followed by an "off" period as non-drug containing layer 124 slowly erodes, thereby exposing drug layer 120 which delivers another drug pulse at t=96 hours, and so forth, until the dispenser is depleted of drug and non-drug containing layers.

Figure 10:
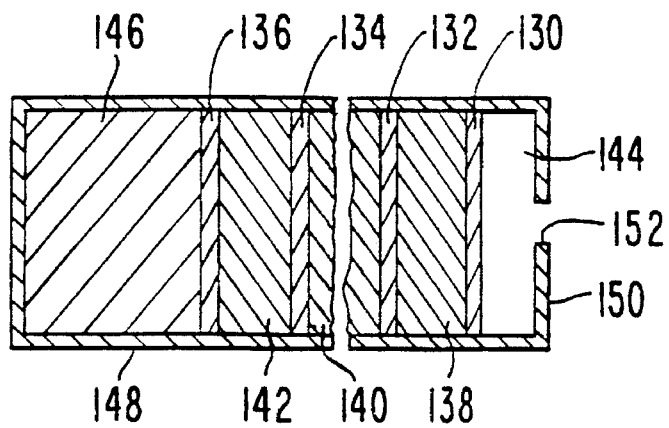
FIG. 10 is a partial cross-sectional view of another embodiment of the dispenser of this invention capable of providing a plurality of drug pulses.

FIG. 10 illustrates another embodiment of the dispenser which provides "off" periods during which no drug is delivered. Delivery programs having an on and off cycle normally require a large dispenser volume. The embodiment of FIG. 10 allows reduction of this large volume requirement by incorporating a gas generator, alone or in combination with an osmotic agent, into the drug layers 130, 132, 134 and 136.

The drug layers are contained in a two part housing unit and are separated by non-osmotically active spacers or placebo layers 138, 140 and 142. The housing is also designed with a volume expansion chamber 144 and a driving member 146. The housing has a first rigid or semi-rigid portion 148 having a low permeability ($k_1\pi_1$) and a second portion or closure 150 having a high permeability ($k_2\pi_2$), where k is the permeability coefficient defined as cc of fluid/hr-cm², and π is the osmotic pressure.

In operation, the presence of a gas generator, with or without an osmotic agent, in the drug layers operates to effect its discharge as a pulse of drug delivered when the layer comes into contact with the "window" (closure 150) of highly permeable membrane in the flow path of the drug layer, said flow path being through a volume expansion chamber 144. Suitable gas generators are disclosed above with reference to FIG. 5.

The driving member 146 is that of FIG. 3, an osmotic agent. Member 146 provides low flux. When drug layer 130 for instance, contacts the volume expansion chamber 144, the gas generator and any osmotic agent contained therein gives the layer with $k_2\pi_2 \gg k_1\pi_1$, which blows out the drug layer and the drug is dispensed to the environment through exit 152.

In an alternate embodiment, spacers 138, 140 and 142 are osmotically active. Both the driving member 146 and these spacers are comprised of a salt or sugar having low osmotic activity and work together to provide a low flux drive. As noted above, when drug layer 130 contacts the high permeability closure 150, the drug is blown out.

The drug delivery program provided by the dispenser of FIG. 10 involves a series of drug pulses separated by a delay or an "off" period. The drug pulse is dependent upon the drug/gas generator/osmotic agent layer contacting the high kπ volume expansion chamber. The delay, on the other hand, is dependent upon the low flux drive provided by member 146.

FIGS. 11–15 illustrate examples of housing structures useful for use with this invention. These structures and suitable materials therefore, are fully disclosed in the coassigned patent application of Magruder et al, Ser. No. 07/283,359, filed Dec. 13, 1988, now U.S. Pat. No. 5,034,229 issued Jul. 23, 1991, incorporated herein by reference. In general terms, the housing embodiments disclosed therein are described as having two walled sections, one substantially impermeable section which defines the dispensing component and one semipermeable section which defines the driving component. The driving component is typically an expandable material such as is described with reference to expandable member 38 in FIG. 2.

Figure 11:
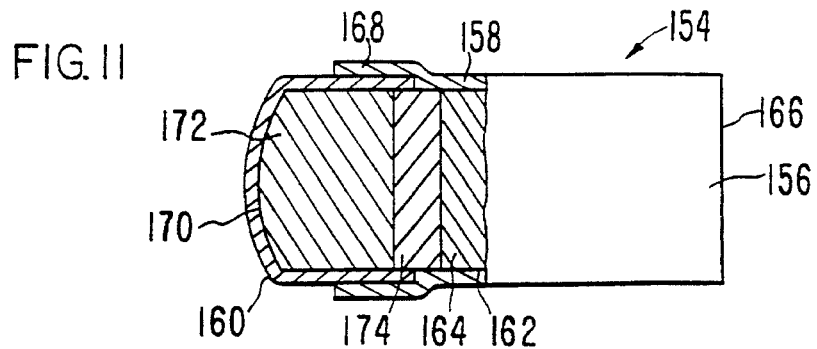
FIG. 11 is a partial cross-sectional view of an embodiment of the housing for the dispenser of this invention, having a first and a second walled section.

FIG. 11 depicts a partial cross-sectional view of delivery system 154, which comprises housing member 156. Housing member 156 comprises a dispensing component identified by first wall section 158 and a driving component identified by second wall section 160, which surround and define an internal compartment 162, which contains a plurality of drug layers, 164 for example. Wall section 158 at its end distant from exit port 166 defines and forms receiving means 168. Receiving means 168 is enlarged slightly for receiving second wall section 160. Wall section 160 surrounds the internal compartment area 170 that contains a driving component 172 which is suited for expanding and for occupying space in compartment 170 for delivery of a plurality of drug layers from delivery system 154. The two wall sections, sections 158 and 160 at receiving end 168, are close in size and they form a tight friction fit therebetween. There is clearance or tolerance in size to allow wall section 160 a sliding movement into the receiving means 168 of wall section 158. Wall section 158 and wall section 160 can be telescoped completely into a closed, and continuous walled position. Optionally, they can be held together by heat fusion, by an adhesive, or the like.

Wall section 158 comprises a composition that is substantially impermeable to the exchange of fluid, drug and other ingredients contained in delivery system 154. Wall section 158, in a presently preferred manufacture, is substantially impermeable to the ingress of an external fluid to serve as a means for substantially protecting drug layers that may contain a drug that is sensitive to fluid from an exterior fluid present in the environment of use. Wall section 158 substantially restricts and prevents fluid from passing through wall 158 and entering into compartment 162 in the region containing drug layers. Wall section 160 comprises in at least a part a semipermeable wall composition that is permeable to the passage of fluid for making available fluid to an expandable driving means 172 inside compartment 170. Wall section 160 is permeable to the passage of fluid and it is substantially impermeable to the passage of other ingredients contained in delivery system 154. Wall sections 158 and 160 optionally comprise a plasticizer that imparts flexibility and workability to the wall. Housing 156, comprising sections 158 and 160, is non-toxic and, in a preferred embodiment, it maintains its physical and chemical integrity, that is, housing 156 does not erode during the dispensing period.

Compartment 162 optionally comprises a layer 174, which is positioned between the drug layer 164 and the driving component 172. Layer 174, in a presently preferred embodiment, comprises a composition that is substantially impermeable to the passage of fluid and it serves to restrict the passage of fluid present in the expandable driving member into the compartment 162 housing the drug layers. Layer 174 further operates to essentially maintain the integrity of the drug layers and the driving component 172. Layer 174 acts also to insure that the expanding driving force generated by the driving component is applied directly against the drug layers. In operation, as the driving component 172 absorbs and imbibes fluid, it expands and pushes against layer 174 causing it to slide inside compartment 158. Layer 174 moves towards exit port 166, pushing the drug layers through exit port 166 for maximizing the delivery of the drug to a biological environment of use, such as livestock.

Figure 12:
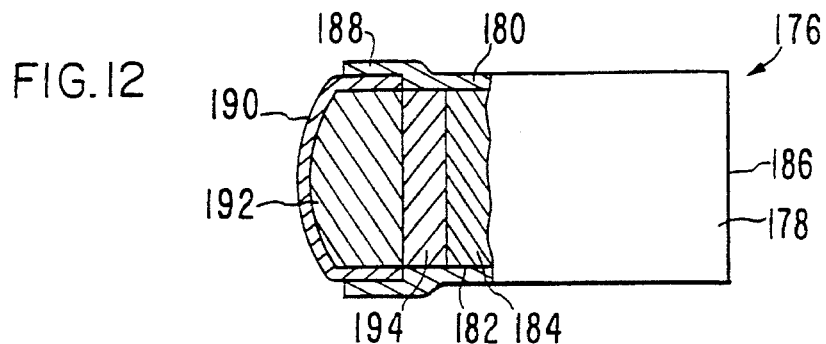
FIG. 12 is a partial cross-sectional view of another embodiment of the housing for the dispenser of this invention with means for releasably holding an insert member comprising an expandable member for pushing layers out of the dispenser.

FIG. 12 is a partial cross-sectional view of another housing embodiment of delivery system 176 provided by the invention. In FIG. 12, delivery system 176 comprises housing member 178, wall 180, and internal compartment 182 that contains a plurality of drug layers 184. In FIG. 12, wall 180 is continuous and it extends the length of delivery system 176. Wall 180, at its end distant from exit port 186, comprises a receiving end 188. Receiving end 188 is designed and adapted for receiving insert 190. Insert 190 is cup-like in shape, or tube-like with a single closed end, and it is made of a composition such as a polymeric composition that is permeable to the passage of an external fluid. Insert 190 comprises a driving component 192 and a layer or partition 194 that separates driving component 192 from the other ingredients present in compartment 182. Insert 190 in end 188, in a presently preferred embodiment, is replaceable and one or more than one insert 190 can be used during the operation of delivery system 176.

Figure 13:
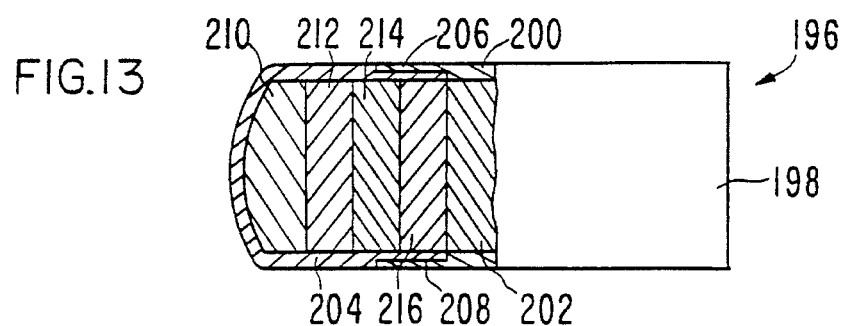
FIG. 13 is a partial cross-sectional view of still another embodiment of the housing having a first walled section and an engaging second walled section.

FIG. 13 is a partial cross-sectional view of delivery system 196 comprises housing member 198 formed by a first wall section 200 that surrounds an internal compartment area containing a plurality of drug layers 202, and a second wall section 204 that surrounds an internal compartment area comprising at least one means for occupying space in the compartment. First wall section 200 is provided with receiving means 206. Wall 200 at receiving means 206 is thinner and it exhibits smaller internal dimensions for receiving second section 204 at its open end 208. Wall section 204 is thinner at its open end 208 and it exhibits smaller external dimensions for sliding into receiving end 206 in mated relation for providing an essentially continuous wall. The two sections can be joined together by various techniques such as solvent weld, adhesive bond, thermal weld, ultrasonic weld, spin weld, induction weld, or by similar welding or bonding operations. First wall section 200 and second wall section 204 in the delivery system 196 seen in FIG. 13 are substantially uniform in cross-sectional dimensions thereby providing delivery system 196 with substantially uniform dimensions along its central axis. In a presently preferred embodiment delivery system 196 comprises a multiplicity of driving components 210, 212 and 214 which may comprise like or unlike compositions. Delivery system 196 in a presently preferred manufacture comprises layer 216 that separates the drug layers 202 from the driving components.

Figure 14:
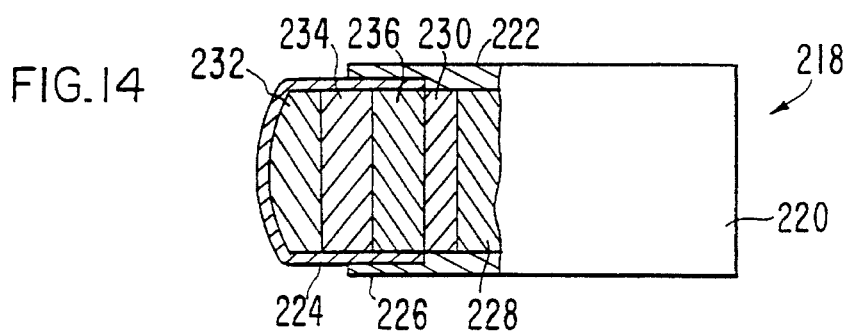
FIG. 14 is a partial cross-sectional view of another embodiment of the housing for the dispenser of this invention having a multi-layer containing section and a driving force section joined as releasable engaging structural member sections.

FIG. 14 is a partial cross-sectional view of delivery system 218, which comprises housing member 220, first wall section 222, second wall section 224, receiving means 226, a plurality of drug layers 228. In FIG. 14, the first wall section 222 functions as a first body portion of delivery system 218, and it is designed for slipping over, or for receiving second wall section 224 that serves as a second body portion. The second body portion is telescopically capped by the engaging first body portion 222. In FIG. 14, delivery system 218 comprises a partition 230 positioned near the drug layers 228 contained within the space defined by first section 222, and at the filling entrance of second section 224 comprises a plurality of driving members 232, 234 and 236. The members are presently formed as depots or layers of the same or different member forming composition selected from the group consisting of expandable materials disclosed herein.

Figure 15:
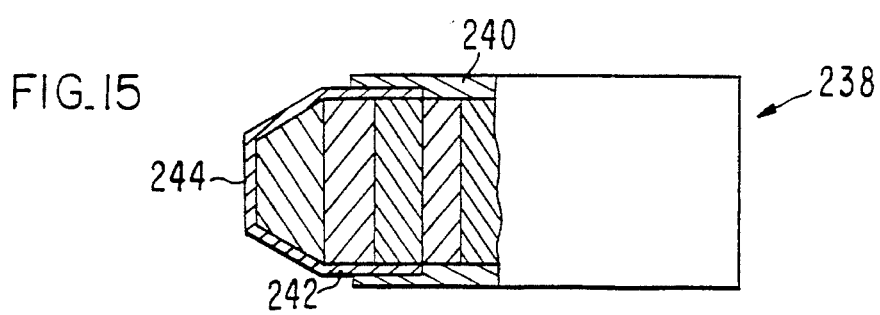
FIG. 15 is a partial cross-sectional view of still another embodiment of the housing where the end is tapered.

In FIG. 15, a dosage form 238 is seen in cross-section, which dosage delivery form 238 is similar in structure and in operation to delivery form 218 illustrated in FIG. 14 and is comprised of a first wall section 240 and a second wall section 242. The second wall section 242 of this embodiment has a tapered end 244, rather than a dome-shaped end.

The amount of drug incorporated in the layers of the dispenser of this invention varies widely depending upon the particular drug, the desired therapeutic effect, and the time span for which it takes the drug to be released. Since a variety of sizes and compositions are intended to provide complete dosage regimes for therapy for a variety of maladies, there is no critical upper limit on the amount of drug incorporated into the layers of the dispenser. The lower limit too will depend upon the activity of the drug and the time span of release from the layers. Thus, it is not practical to define a range for the therapeutically effective amount of drug to be released by the individual layers, or by the dispenser as a whole.

The following examples are merely illustrative of the present invention and they should not be considered as limiting the scope of the invention in any way as these examples and other equivalents thereof will become apparent to those versed in the art in the light of the present disclosure, the drawings and the accompanying claims.

EXAMPLE III

A delivery system manufactured in the shape of a drug dispenser comprising a dispensing component with an exit port and a driving component, is manufactured as follows: first, an expandable driving member is prepared by adding 9.5 liters of water and 500 g of polyvinyl pyrrolidone to a stainless steel container and the components mixed for 20 hours to obtain a smooth, binder solution. Next, 34.6 kg of sodium Carbomer®, a sodium salt of polyacrylic acid polymer, is sized by forcing it through a 0.028 inch mesh screen in a fluid air mill set at 780–800 rpm speed. Then, 33 kg of the screened polymer is transferred to the granulator bowl of a fluid bed granulator and 6.6 liters of the binder solution is slowly sprayed onto the polymers in the granulator. The polymer granules are formed in this manner.

Next, 15 kg of sodium chloride is milled in a mill to a number 21 size mesh screen. Then, 31.32 kg of the granules of sodium Carbomer® is mixed with 13.68 kg of the milled sodium chloride and the mix blended for about an hour. Then 455 g of magnesium stearate is added and the ingredients blended for 10 minutes to produce a homogeneous expandable driving composition. The composition next is pressed into osmotically active tablets in a tablet press at a pressure of 500 lbs to produce a round, flat faced 30 mg tablet.

The driving component is comprised of a semipermeable wall that surrounds a compartment for containing the osmotically active tablet. This wall is prepared as follows: first, 3.85 kg of cellulose acetate butyrate and 1.15 kg of tributyl citrate are dry mixed in a mixer for 5 minutes. This produces a polymer plasticizer blend of a 77/23 ratio for the semipermeable wall. Next, a rubber mill is used to melt blend the blend, at a roller temperature of 70° C. The blend is transferred to the moving rollers of the mill and mixed for 3 minutes. Then, after all the materials are added to the mill, the temperature is raised to 90° C., followed by milling for 2 minutes, next the temperature is raised to 115° C. and followed by two more minutes of milling, then the temperature is increased to 133° C. and followed by six minutes of milling the blend, and then the temperature is increased to 144° C. and followed by six minutes of milling the blend. After the rollers are cooled to 50° C., the blend is removed from the mill. The milled blend is cut into strips and passed through a grinder mill, and the resulting particles fed into an injection molder and molded into the semipermeable wall surrounding a compartment with an opened end for receiving an expandable driving member and for mating with the dispensing component of the delivery system.

Next, the dispensing component of the delivery system is prepared by adding 5 kg of polycarbonate to a hopper dryer and drying the polymer at 250° F. for 4 hours. Then the dry polymer is fed into the hopper of an injection molder, where a single cavity hot tip mold is used to injection mold an impermeable wall surrounding a compartment with one open end for receiving the drug layers and for mating with the semipermeable wall member, and a second open end which forms the exit port.

Next, the delivery system is assembled by first charging the subassembly (driving component) semipermeable walled member with three osmotic tablets. Then, microcrystalline wax is melted and the molten wax poured on the top of the osmotic tablets to completely fill to the opened walled member. The charged subassembly is allowed to cool to room temperature.

Next, the delivery system subassembly (dispensing component) comprising the substantially impermeable wall surrounding the compartment is filled with a plurality of drug layers having the following composition: 85 wt % porcine somatotropin, 2 wt % polyvinyl pyrrolidone, 1 wt % magnesium stearate, 3 wt % hydrogenated vegetable oil, 5 wt % Polyox® (polyethylene oxide) and 4 wt % histadine HCl. A suitable dosage of porcine somatotropin is about 112 mg per system. Therefore, the size and number of layers will be designed accordingly. Then, the two subassemblies at their opened ends are joined by inserting partially the member comprising the osmotic tablets and the wax, into the member comprising the drug layers, Next, 4 drops of moisture-cured cyanoacrylic adhesive are dropped into the remaining exposed surface, the two members fully inserted and then twisted to effect a completed delivery system.

EXAMPLE IV

A dispenser according to Example III is prepared. The drug layer composition is: 88 wt % porcine somatotropin, 2 wt % polyvinyl pyrrolidone, 1 wt % magnesium stearate, 5 wt % Polyox® and 4 wt % histadine HCl. The hydrogenated vegetable oil is eliminated from the layer composition and instead, about 50 πl is injected into the dispensing component. The dispensing component is then filled with the drug layers and the subassemblies joined as in Example III.

EXAMPLE V

A dispenser according to Example III is prepared. When the dispensing component is being filled with the drug layers, inert wax spacers are positioned alternating with the drug containing layers and the subassemblies joined as in Example III.

METHOD OF USING THE INVENTION

The dispenser of the invention can be used according to the following methods to produce a beneficial effect on animals including humans. The method comprises admitting orally, implanting, in a body passageway, subdermally, or by surgery, a dispenser comprising:

(a) a housing;

(b) an inlet in the housing;

(c) an outlet in the housing;

(d) means in the housing for generating a gas pressure for moving a drug formulation from the dispenser, said means comprising a gas generating formulation positioned at the inlet for receiving fluid that enters the dispenser;

(e) a drug formulation in the housing, which drug formulation when moved by the gas pressure to a contacting fluid at the outlet of the dispenser; erodes over time; and (f) an inert formulation in the housing in contacting arrangement with the drug formulation, which inert formulation is a means for enabling the drug formulation to be delivered as a unit dose over time to the environment; and wherein the method:

(g) delivers the drug formula to the animal at a beneficially effective dose over time.

The method comprises also admitting into the animal a different dispenser comprising:

(a) a housing;

(b) an inlet in the housing;

(c) an outlet in the housing;

(d) means in the housing for pumping a member selected from the group consisting of a solution and suspension against a drug formulation for moving a drug formulation through the outlet from the dispenser, said means comprising a semipermeable wall that surronds a core that provides a fluid member selected from the group consisting of a solution and a suspension, with an orifice in the semipermeable wall for directing the fluid membrane towards a drug formulation;

(e) a drug formulation in the housing, which drug formulation performs by at least one of dissolving and eroding over time when pushed by fluid member towards the outlet of the dispenser; and, (f) an inert formulation in the housing in contacting arrangement with the drug formulation, which inert formulation is a means for effecting the delivery of the drug formulation as a unit dose of drug to the environment; and, wherein the method comprises:

(g) delivering the drug formulation from the dispenser at a rate of 10 nanograms to 25 grams per day for up to 180 days; to produce a therapeutic drug benefit.

This invention has been described in detail with particular reference to certain perferred embodiments thereof, but it will be understood that variations and modifications can be effected within the spirit and scope of the invention.

What is claimed:

1. A dispenser for delivering a drug to an environment comprising a fluid, the dispenser comprising:

(a) a housing;
   (b) an inlet in the housing;
   (c) an outlet in the housing;
   (d) a plurality of longitudinally aligned layers in the housing comprising;
   (e) a drug formulation layer, which drug formulation layer erodes over time when moved by the gas pressure to a contacting fluid at the outlet of the dispenser,
   (f) an inert formulation layer in contacting arrangement with the drug formulation layer, which inert formulation layer is a means for enabling the drug formulation layer to be delivered as a unit dose over time to the environment; and,
   (g) a gas generating formulation layer in the housing for generating a gas pressure for moving the drug formulation layer and the inert formulation layer out of the dispenser at a rate that is solely governed by the rate of fluid that enters the housing and the gas generated, said gas generating formulation layer positioned at the inlet in the housing for receiving fluid that enters the dispenser.

2. The dispenser for delivering the drug according to claim 1, wherein said drug in the drug formulation layer is selected from the group consisting of pharmacologically active peptides, protein anabolic hormones, growth promoting hormones related to the endocrine system, porcine growth promoting hormone, bovine growth promoting hormone, equine growth promoting hormone, ovine growth promoting hormone, human growth promoting hormone, growth promoting hormones derived by extraction and concentration from pituitary and hypothalamus glands, growth promoting hormones produced by recombinant DNA methods, polypeptides, growth hormone, somatropin, somatotropin, somatomedin-C, gonadotropin releasing hormone, follicle stimulating hormone, luteinizing hormone, LH-RH, growth hormone releasing factor, gonadotropin releasing factor, insulin, colchicine, chorionic gonadotropin, oxytocin, vasopressin, adrenocorticotrophic hormone, epidermal growth factor, prolactin, somatostatin, cosyntropin, lypressin, thyrotropin releasing hormone, thyroid stimulating hormone, secretin, pancreozymin, enkephalin, and glucagon.

3. A dispenser for delivering a drug to an environment comprising a fluid, the dispenser comprising:

(a) a housing;
   (b) an inlet in the housing;
   (c) an outlet in the housing;
   (d) a plurality of longitudinally aligned layers in the housing, comprising;
   (e) a drug formulation layer, which drug formulation layer dissolves over time when pushed by the hydropressure to a contacting fluid at the outlet of the dispenser,
   (f) an inert formulation layer in contacting arrangement with the drug formulation layer, which inert formulation layer is a means for effecting the delivery of the drug formulation layer as a unit dose of drug to the environment; and
   (g) a hydropressure generating layer in the housing, said hydropressure generating layer positioned at the inlet in the housing and comprising a material selected from the group consisting of an osmotically effective solute or a fluid-swellable polymer, wherein said hydropressure generating layer increases in dimension and pushes the inert formulation layer and the drug formulation layer through the outlet in the housing at a rate that is solely controlled by the rate of fluid imbibed by the hydropressure generating layer.

4. The dispenser for delivering the drug according to claim 3, wherein the drug in the drug formulation layer is selected from the group consisting of pharmacologically active peptides, protein anabolic hormones, growth promoting hormones related to the endocrine system, porcine growth promoting hormone, bovine growth promoting hormone, equine growth promoting hormone, ovine growth promoting hormone, human growth promoting hormone, growth promoting hormones derived by extraction and concentration from pituitary and hypothalamus glands, growth promoting hormones produced by recombinant DNA methods, polypeptides, growth hormone, somatropin, somatotropin, somatomedin-C, gonadotropin releasing hormone, follicle stimulating hormone, luteinizing hormone, LH-RH, growth hormone releasing factor, gonadotropin releasing factor, insulin, colchicine, chorionic gonadotropin, oxytocin, vasopressin, adrenocorticotrophic hormone, epidermal growth factor, prolactin, somatostatin, cosyntropin, lypressin, thyrotropin releasing hormone, thyroid stimulating hormone, secretin, pancreozymin, enkephalin, and glucagon, which drug is delivered at a rate of delivery greater than the rate the hydropressure pushes the drug formulation layer in the dispenser.

5. A dispenser for delivering a drug to an environment comprising a fluid, the dispenser comprising:

(a) a housing;
   (b) an inlet in the housing;
   (c) an outlet in the housing;
   (d) a plurality of longitudinally aligned layers in the housing comprising;
   (e) a drug formulation layer, which drug formulation layer performs by at least one of dissolving or eroding over time when pushed towards the outlet of the dispenser,
   (f) an inert formulation layer in contacting arrangement with the drug formulation layer, which inert formulation layer is a means for effecting the delivery of the drug formulation layer as a unit dose of drug to the environment; and,
   (g) an osmotic layer positioned at the inlet in the housing, said osmotic layer comprising a semipermeable wall that surrounds a core, said core comprising a material selected from the group consisting of a solution and a suspension, said semipermeable wall comprising an orifice oriented towards the outlet in the housing for directing said core material towards the drug formulation layer for moving the drug formulation layer through the outlet in the housing at a controlled rate over time, said rate solely governed by the osmotic layer.

6. The dispenser for delivering the drug according to claim 5, wherein the drug in the drug formulation layer is selected from the group consisting of pharmacologically active peptides, protein anabolic hormones, growth promoting hormones related to the endocrine system, porcine growth promoting hormone, bovine growth promoting hormone, equine growth promoting hormone, ovine growth promoting hormone, human growth promoting hormone, growth promoting hormones derived by extraction and concentration from pituitary and hypothalamus glands, growth promoting hormones produced by recombinant DNA methods, polypeptides, growth hormone, somatropin, somatotropin, somatomedin-C, gonadotropin releasing hormone, follicle stimulating hormone, luteinizing hormone, LH-RH, growth hormone releasing factor, gonadotropin releasing factor, insulin, colchicine, chorionic gonadotropin, oxytocin, vasopressin, adrenocorticotrophic hormone, epidermal growth factor, prolactin, somatostatin, cosyntropin, lypressin, thyrotropin releasing hormone, thyroid stimulating hormone, secretin, pancreozymin, enkephalin, and glucagon.

* * * * *